United States Patent [19]
Cheung et al.

[11] Patent Number: 5,866,735
[45] Date of Patent: Feb. 2, 1999

[54] HYDROCARBON HYDROGENATION PROCESS

[75] Inventors: Tin-Tack Peter Cheung; Marvin M. Johnson, both of Bartlesville, Okla.

[73] Assignee: Phillips Petroleum Company, Bartlesville, Okla.

[21] Appl. No.: 867,872

[22] Filed: Jun. 4, 1997

Related U.S. Application Data

[63] Continuation-in-part of Ser. No. 595,326, Feb. 1, 1996, abandoned.

[51] Int. Cl.$^6$ .............................. C07C 5/05; C07C 5/08; C07C 7/167
[52] U.S. Cl. .................. 585/273; 585/259; 585/260; 585/261; 585/275; 585/277
[58] Field of Search ........................ 589/290, 259, 589/261, 271, 262, 273, 275; 585/277, 260

[56] References Cited

U.S. PATENT DOCUMENTS

| | | | |
|---|---|---|---|
| 3,878,260 | 4/1975 | Kunugi et al. | 260/680 E |
| 3,932,548 | 1/1976 | Rausch | 260/668 D |
| 4,113,970 | 9/1978 | Tanabe et al. | 560/244 |
| 4,341,912 | 7/1982 | Takahashi et al. | 585/443 |
| 4,435,607 | 3/1984 | Imai | 585/443 |
| 4,717,781 | 1/1988 | Imai et al. | 585/441 |
| 5,057,206 | 10/1991 | Engel et al. | 208/143 |
| 5,475,173 | 12/1995 | Cheung et al. | 585/259 |
| 5,488,024 | 1/1996 | Cheung et al. | 502/325 |
| 5,489,565 | 2/1996 | Cheung et al. | 502/325 |
| 5,583,274 | 12/1996 | Cheung et al. | 585/261 |
| 5,585,318 | 12/1996 | Johnson et al. | 502/330 |
| 5,587,348 | 12/1996 | Brown et al. | 502/230 |

*Primary Examiner*—Bekir L. Yildirim
*Attorney, Agent, or Firm*—Lucas K. Shay

[57] ABSTRACT

A supported hydrogenation catalyst composition is disclosed which comprises a palladium component, at least one alkali metal iodide such as, for example, potassium iodide and an inorganic support material such as alumina. Also disclosed is selective hydrogenation process in which diolefins and/or alkynes are hydrogenated with hydrogen to this corresponding monoolefins.

31 Claims, 2 Drawing Sheets

5,866,735

HYDROCARBON HYDROGENATION PROCESS

This application is a continuation-in-part of application Ser. No. 08/595,326 filed Feb. 1, 1996, now abandoned.

FIELD OF THE INVENTION

This invention relates to a supported noble metal catalyst composition and to a process for selectively hydrogenating diolefins (alkadienes) and alkynes to monoolefins (alkenes) employing a supported noble metal catalyst composition.

BACKGROUND OF THE INVENTION

Catalysts comprising palladium and a support material are known catalysts for dienes and/or alkynes hydrogenation. Even though these catalysts are effective hydrogenation catalysts, some such catalysts tend to produce green oil by oligomerizing the alkynes and dienes. The green oil has 6 or more carbons per molecule and is not desirable in the production of an alkene such as, for example, ethylene because it fouls the catalyst and cuts the yield to alkene. Therefore, there is an ever present need for further improvements of a selective hydrogenation process to achieve enhanced selectivity to monoolefins, or increased catalyst life, or both. Accordingly, development of a modified supported palladium catalyst composition and its use in processes for the selective hydrogenation of diolefins (alkadienes) or alkynes to monoolefins (alkenes) would be a significant contribution to the art.

SUMMARY OF THE INVENTION

It is an object of this invention to provide an improved palladium-containing composition which can be useful as a catalyst in the selective hydrogenation of diolefins and/or alkynes to monoolefins. It is another object of this invention to employ this improved catalyst composition in the selective hydrogenation of diolefins or alkynes to monoolefins. It is also an object of this invention to employ this improved catalyst composition in the selective hydrogenation of alkadienes and alkynes to the corresponding alkenes. It is still an object of this invention to employ this improved catalyst composition in the selective hydrogenation of cyclopentadienes to cyclopentene. It is a further object of this invention to employ this improved composition in the selective hydrogenation of dicyclopentadiene to at least one dihydrodicyclopentadiene. Other objects and advantages will be apparent from the detailed description and the appended claims.

In accordance with the a embodiment of this invention, a catalyst composition is provided which consists essentially of (a) at least one palladium-containing material selected from the group consisting of palladium metal and palladium oxides, (b) at least one alkali metal iodide and (c) at least one inorganic support material. The inorganic support can be a spinel, alumina, silica, titania, zirconia, aluminosilicates, or mixtures of two or more thereof.

In accordance with a second embodiment this invention, a process which can be used for selectively hydrogenating a highly unsaturated hydrocarbon to a less unsaturated hydrocarbon is provided. The process comprises contacting a highly unsaturated hydrocarbon with hydrogen, in the presence of a catalyst composition, under a condition sufficient to effect a selective hydrogenation of the highly unsaturated hydrocarbon. The catalyst composition can be the same as the composition disclosed in the first embodiment of this invention.

DETAILED DESCRIPTION OF THE INVENTION

Figure 1:
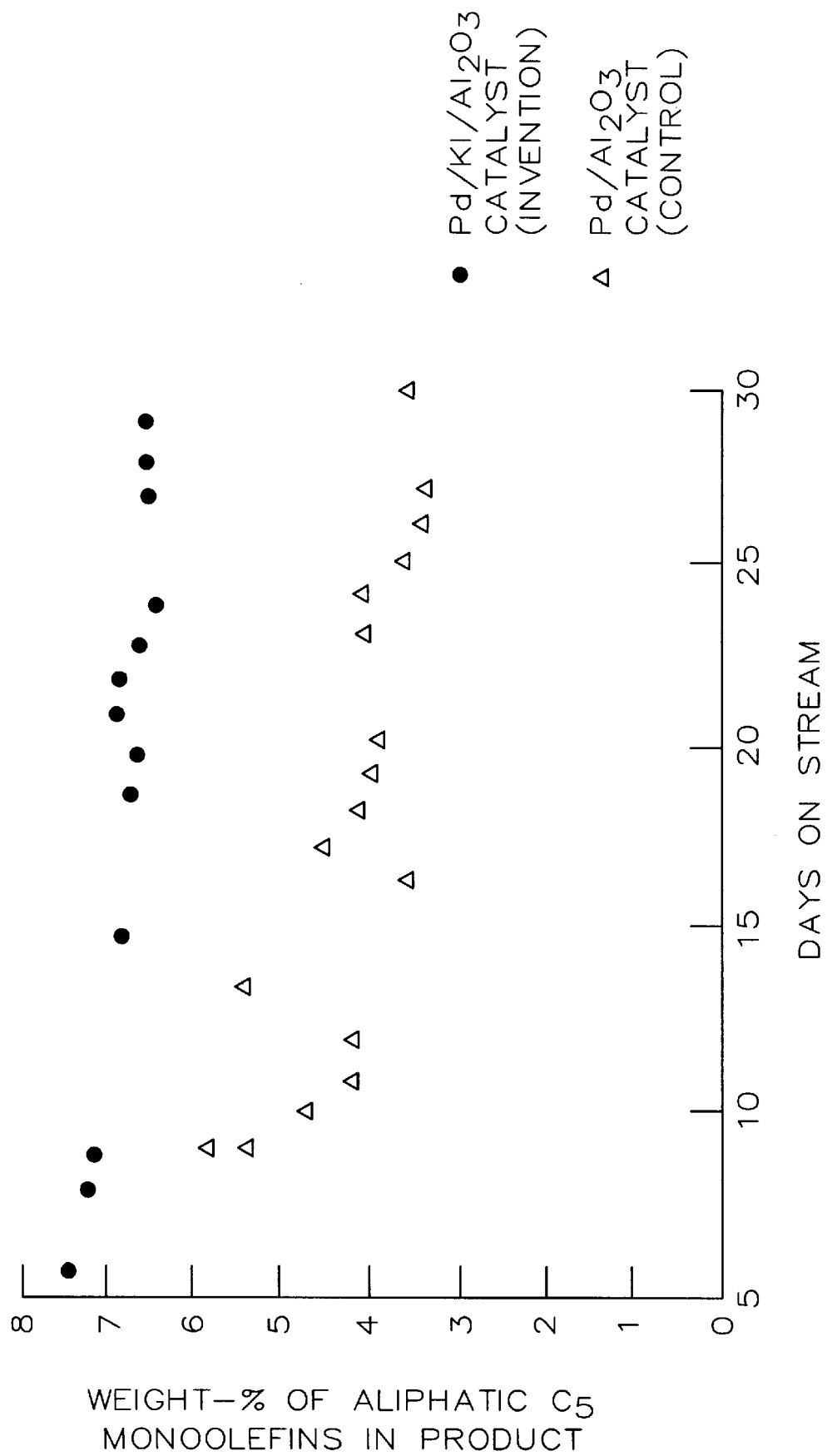
FIG. 1 illustrates the advantages of an invention catalyst over a control catalyst in the selective hydrogenation of diolefins to monoolefins.

As used in the present invention, the term "fluid" denotes gas, liquid, or combination thereof. The term "saturated hydrocarbon" is referred to as any hydrocarbon which can be converted to an unsaturated hydrocarbon such as an olefinic compound by a thermal cracking process. An "unsaturated hydrocarbon" as used in this application is a hydrocarbon having at least one double bond between carbon atoms in the molecule. Generally, example of saturated hydrocarbons include, but are not limited to, ethane, propane, butanes, pentanes, hexanes, octanes, decanes, naphtha, and combinations of any two or more thereof. Examples of unsaturated hydrocarbons include, but are not limited to, monoolefins such as ethylene, propylene, butenes, pentenes, hexenes, octenes, and decenes; aromatic compounds such as naphthalene; alkynes such as acetylene, propyne, and butynes; diolefins such as propadiene, butadienes, pentadienes (including isoprene), hexadienes, octadienes, and decadienes; and combinations of two or more thereof. The term "highly unsaturated hydrocarbon" refers to a hydrocarbon which contains a triple bond or two or more double bonds in a molecule. The term "less unsaturated hydrocarbon" refer to a hydrocarbon in which the triple bond in the highly unsaturated hydrocarbon is hydrogenated to a double bond or a hydrocarbon in which the number of double bonds is one less than that in the highly unsaturated hydrocarbon. The term "selective hydrogenation" is referred to as a hydrogenation process which converts a highly unsaturated hydrocarbon such as an alkyne or a diolefin to a less unsaturated hydrocarbon such as a monoolefin without hydrogenating the less unsaturated hydrocarbon to a saturated or a more saturated hydrocarbon such as alkane.

The composition of matter of this invention consists essentially of (a) palladium metal and/or at least one palladium oxide, (b) at least one alkali metal iodide (preferably potassium iodide), and (c) an inorganic support material selected from the group consisting of alumina, silica, titania, zirconia, aluminosilicates (clays and/or zeolites), zinc aluminate, zinc titanate, and mixtures of two or more than two of these compounds, preferably alumina, more preferably alpha-alumina. Generally, the catalyst composition contains about 0.01–2 (preferably about 0.05–1) weight % Pd and about 0.02–10 (preferably about 0.05–5) weight % alkali metal (preferably K). The catalyst particles can have any suitable shape (spherical, cylindrical, trilobal and the like), and are preferably either spherical pellets or cylindrical extrudates. The catalyst particles can have any suitable particle size (diameter/length), and generally have a size of about 1–10 mm (preferably about 2–6 mm). The catalyst particles can have any suitable surface area (measured by the BET method by Brunauer, Emmett and Teller employing $N_2$), and generally have a surface area of about 1–200 (preferably about 5–100) $m^2/g$.

The catalyst particles can be prepared by any suitable means. The promoter components (a) and (b) can be deposited onto and/or incorporated into the inorganic support material by any suitable means and in any suitable order. For instance, the alkali metal iodide can be incorporated into the support material, by impregnation, followed by impregnation of the alkali metal iodide-containing support material with at least one Pd compound (such as $H_2PdCl_4$), drying and then heating (calcining) of the thus-impregnated composition (preferably in a reducing gas atmosphere such as hydrogen gas, or in an inert gas atmosphere such as nitrogen, helium and the like). Or a supported palladium catalyst composition, preferably a $Pd/Al_2O_3$ composition (more preferably one which is commercially available, e.g., from Mallinckrodt Specialty Chemicals Company, Erie, Pa.), can be impregnated with an alkali metal iodide, followed by drying and then heating (preferably in a reducing or inert gas atmosphere) of the thus-impregnated composition. Or the supported palladium catalyst composition can be impregnated with at least one alkali metal iodate, followed by drying and then heating the impregnated material in a reducing gas atmosphere, preferably hydrogen gas (at a temperature sufficient to convert the alkali metal iodate to alkali metal iodide). The palladium component can also be present as "skin", i.e., distributed on the surface of the catalyst particle or support.

The preferred starting material (also referred to as "base catalyst"), which is to be improved in accordance with this invention by incorporation of alkali metal iodide therein, can be any supported palladium-containing composition. The base catalyst composition can be a fresh hydrogenation catalyst or it can be a used and thereafter regenerated hydrogenation catalyst composition. The base catalyst composition can also be a shell or skin catalyst in which the palladium is present in a thin layer at the outside surface of the catalyst particles or support. Broadly, the base catalyst can contain about 0.01–2 (preferably about 0.05–1) weight % Pd, and a solid inorganic support material (listed above), preferably alumina (more preferably alpha-alumina). The supported Pd-containing base catalyst particles can have any suitable shape, and preferably are spherical pellets or cylindrical extrudates. The size of these supported base catalyst particles generally is about 1–10 mm, preferably about 2–6 mm, and its surface generally is about 1–200 $m^2/g$.

In one preferred method of preparing the catalyst composition of this invention, a Pd-containing base catalyst (described above), which more preferably has been prereduced with hydrogen gas at room temperature (about 10°–40° C.), is contacted with a solution (preferably aqueous) of at least one alkali metal iodide (preferably KI) at such conditions as to obtain a final catalyst composition containing about 0.02–10 (preferably about 0.05–5) weight % of alkali metal (preferably potassium). Generally, the concentration of the alkali metal iodide in the contacting (impregnating) solution (preferably aqueous) is about 0.02–10 mol/l (preferably about 0.2–3 mol/l). The preferred contacting method is "incipient wetness impregnation", i.e. essentially completely filling the pores of the base catalyst with the alkali metal iodide solution. Generally, the weight ratio of the solution to the solid base catalyst composition is in the range of about 0.2:1 to about 2:1, preferably about 0.4:1 to about 1:1 (depending on the alkali metal iodide concentration of the impregnating solution and the desired alkali metal iodide level to be attained in the catalyst composition of this invention). Thereafter, the impregnated catalyst composition is substantially dried (preferably at about 50°–150° C. for about 0.5–20 hours) and heated in a non-oxidizing gas atmosphere (more preferably in a reducing gas such as $H_2$, or an inert gas such as $N_2$, He and the like) at a temperature of about 300°–600° C. (preferably about 300°–500° C.) for a time period of about 0.2–20 hours (preferably about 1–10 hours).

In another preferred method of preparing the catalyst composition of this invention, a Pd-containing base catalyst (described above) is contacted with a solution (preferably aqueous) of at least one alkali metal iodate (preferably $KIO_3$) at such conditions to obtain a final catalyst composition containing about 0.02–10 (preferably about 0.05–5) weight % alkali metal (preferably K), wherein the concentration of the alkali metal iodate(s) in the impregnating solution is about 0.02–10 mol/l (preferably about 0.2–3 mol/l). The impregnating procedure is carried out essentially in accordance with the method described above for the impregnation with alkali metal iodide. Thereafter, the impregnated catalyst composition is substantially dried (as described above) and heated in a reducing gas (preferably $H_2$) at a temperature of about 200°–600° C. (preferably about 300°–500° C.) for a time period of about 0.2–20 hours (preferably 1–10 hours) so as to convert said at least one alkali metal iodate to at least one alkali metal iodide.

The selective hydrogenation process of this invention can be carried out by contacting a fluid which comprises a highly unsaturated hydrocarbon, in the presence of hydrogen, with the catalyst composition disclosed above. Preferably the fluid containing a highly unsaturated hydrocarbon is or comprises an unsaturated alkene stream containing an alkyne, a diolefin, or both as an impurity, generally at a level of about 1 mg/Kg (ppm) to about 50,000 ppm of the fluid. The unsaturated alkene in the fluid can be ethylene, propylene, butenes, or combinations of two or more thereof. The highly unsaturated hydrocarbon can be, for example, an alkyne, a diolefin, or combinations of any two or more thereof. Examples of suitable alkynes include, but are not limited to, acetylene, propyne, 1-butyne, 2-butyne, 1-pentyne, 2-pentyne, 3-methyl-1-butyne, 1-hexyne, 1-heptyne, 1-octyne, 1-nonyne, 1-decyne, and mixtures of two or more thereof. The presently preferred alkyne is acetylene. These alkynes are primarily hydrogenated to the corresponding alkenes. For example, acetylene is primarily hydrogenated to ethylene, propyne is primarily hydrogenated to propylene, and the butynes are primarily hydrogenated to the corresponding butenes (1-butene, 2-butenes). Similarly, in the selective hydrogenation of diolefins, the diolefins are hydrogenated to the corresponding monoolefins such as, for example, 1,3-butadiene is hydrogenated to butenes and are selectively hydrogenated to pentenes.

The catalyst composition of this invention can be employed directly in the selective hydrogenation process of the second embodiment of this invention. However, it is preferred to first treat the catalyst composition with a reducing gas such as hydrogen. Generally, the optimal operation of the selective hydrogenation does not begin until there has been a substantial reduction of the palladium component. Typically, the reduction can be carried out at a temperature in the range of about 10° C. to about 200° C., preferably 20° to 100° C., for at least 10 minutes, preferably about 0.5 to about 10 hours, and most preferably 1 to 10 hours.

Non-limiting examples of suitable diolefins, preferably containing 3–12 carbon atoms per molecule which can be hydrogenated in the process of this invention include propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes dimethylcyclopentadienes, ethylcyclopentadienes, dicyclopentadiene, and mixtures of one or two of these diolefins. Presently preferred diolefins are propadiene, 1,3-butadiene, pentadienes (such as 1,3-pentadiene, 1,4-pentadiene, isoprene), cyclopentadienes (such as 1,3-cyclopentadiene) and dicyclopentadiene (also known as tricyclo[5.2.1]$^{2,6}$deca-3,8-diene). These diolefins are selectively hydrogenated to the monoolefins containing the same number of carbon atoms per molecule as the diolefins. For example, 1,3-butadiene is hydrogenated to 1-butene and 2-butene, 1,3-pentadiene and 1,4-pentadiene are hydrogenated to 1-pentene and 2-pentene, isoprene is hydrogenated to methyl-1-pentenes and methyl-2-pentenes, 1,3-cyclopentadiene is hydrogenated to cyclopentene, and dicyclopentadiene is hydrogenated to dihydrocyclopentadienes (in particular, tricyclo[5.2.1]$^{2,6}$dec-3-ene).

The highly unsaturated hydrocarbon-containing fluid feed for the hydrogenation process of this invention can also comprise other hydrocarbons, in particular, monoolefins and aromatic hydrocarbons. Non-limiting examples of such other hydrocarbons which can be present in the feed at a level of at least 30 volume % include, but are not limited to, ethylene, propylene, 1-butene, 2-butene, isobutylene, 1-pentene, 2-pentene, methyl-1-butenes (such as 2-methyl-1-butene), methyl-2-butenes (such as 2-methyl-2-butene), 1-hexene, 2-hexene, 3-hexene, methyl-1-pentenes, 2,3-dimethyl-1-butene, 1-heptene, 2-heptene, 3-heptene, methyl-1-hexenes, methyl-2-hexenes, methyl-3-hexenes, dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentene, cycloheptene, methylcyclohexene, dimethylcyclopentenes, ethylcyclopentenes, cyclooctenes, methylcycloheptenes, dimethylcyclohexenes, ethylcyclohenenes, trimethylcyclohexenes, methylcyclooctenes, dimethylcyclooctenes, ethylcylcooctenes, benzene, toluene, ethylbenzene, styrene, xylenes and the like, and mixtures of two or more than two of these hydrocarbons.

The fluid feed which may be liquid or gaseous at the hydrogenating conditions of this process generally comprises about 0.1 to about 99.9 weight % of at least one diolefin. The fluid feed can additionally comprise other hydrocarbons (at a level of about 0.1–99.9 weight %), in particular aromatic hydrocarbons, such as benzene, toluene, styrene and ethylbenzene, which may be present at a level of about 50–99 weight %. However, it is within the scope of this invention to employ feeds which contain about 100% of at least one diolefin, such as substantially pure dicyclopentadiene. Also, the feed can contain small amounts, generally less than about 0.05 weight %, in particular about 10–400 ppm S, of sulfur compounds (such as $H_2S$, carbonyl sulfide, carbon disulfide, mercaptans, organic sulfides such as thiophene, organic di-, tri- and tetrasulfides, and the like) as impurities. Carbon monoxide and/or water (generally less than about 0.05 mole-% of each) can also be present as impurities.

The selective hydrogenation process of this invention is generally carried out by contacting a feed stream containing at least one highly unsaturated hydrocarbon and molecular hydrogen with the catalyst of this invention which is generally contained in a fixed bed. Generally, about 1 to about 10, preferably about 1 to about 2, moles of hydrogen are employed for each mole of the highly unsaturated hydrocarbon present in the feed. The temperature necessary for the selective hydrogenation process of this invention depends largely upon the activity of the catalyst and the desired extent of diolefin hydrogenation. Generally, reaction temperatures in the range of from about 10° C. to about 300° C., preferably about 20° C. to about 250° C., and most preferably 30° C. can be used. A suitable reaction pressure generally is in the range of about 15 to about 2,000 pounds per square inch gauge (psig), preferably 50 to about 1,500 psig, and most preferably 100 to 1,000 psig. The liquid hourly space velocity (LHSV) of the hydrocarbon feed can vary over a wide range. Typically, the space velocity of the feed will be in the range of about 0.5 to about 100 liters of hydrocarbon feed per liter of catalyst per hour, more preferably about 2 to about 60 liters/liter/hour. The hydrogenation process conditions should be such as to avoid significant hydrogenation of monoolefins which are formed by hydrogenation of the highly unsaturated hydrocarbons being initially present in the feed to saturated hydrocarbons such as alkanes and cycloalkanes.

In a preferred embodiment, the at least one alkadiene is selected from the group consisting of propadiene, 1,3-butadiene, 1,3-pentadiene, 1,4-pentadiene and isoprene are selectively hydrogenated with hydrogen gas to at least one alkene selected from the group consisting of butenes and pentenes in the presence of the catalyst composition of this invention. In another preferred embodiment, 1,3-cyclopentadiene is selectively hydrogenated with hydrogen gas to cyclopentene in the presence of the catalyst composition of this invention. In still another preferred embodiment, dicyclopentadiene is selectively hydrogenated with hydrogen gas to at least one dihydrodicyclopentadiene in the presence of the catalyst composition of this invention.

In one of the preferred embodiments of the diolefin hydrogenation process of this invention, a feed stream containing at least one pentadiene, such as, for example, 1,3-pentadiene and/or 1,4-pentadiene and/or isoprene and molecular hydrogen is contacted with the catalyst, generally contained in a fixed bed. Generally, the hydrocarbon feed contains other hydrocarbons, such as $C_4$+ alkanes (butanes, pentanes, hexanes), $C_4$+ alkenes (butenes, pentenes, hexenes) and aromatic hydrocarbons (benzene, toluene, ethylbenzene, styrene and the like). This preferred hydrogenation process generally employs about 1 to about 2 moles of $H_2$ per mole of pentadiene(s). The reaction temperature necessary for the selective hydrogenation of pentadiene depends largely upon the activity of the catalyst and the desired extent of the pentadiene hydrogenation, and generally is in the range of about 35° C. to about 100° C. Generally, the total pressure is in the range of about 50 to 1,000 pounds per square inch gauge (psig). The liquid hourly space velocity (LHSV) of the hydrocarbon feed can also vary over a wide range. Typically, the liquid hourly space velocity will be about 1 to about 50 liter/liter/hour. The hydrogenation process conditions should be such as to avoid significant hydrogenation of pentenes to pentane.

In another preferred embodiment, dicyclopentadiene is selectively hydrogenated to dihydrodicyclopentadienes, mainly the dicyclopentene containing the double bond in the "3" position (i.e., tricyclo[5.2.1]$^{2,6}$dec-3-ene). In still another preferred embodiment, 1,3-butadiene is selectively hydrogenated to butenes. Operating conditions for these embodiments are substantially the same as those described above for the selective hydrogenation of pentadiene(s) to pentenes.

Also within the scope of this invention is to employ the catalyst composition in accordance with this invention for the selective hydrogenation of alkynes, preferably containing 2–12 carbon atoms, to the corresponding monoolefins (alkenes). The reaction conditions for the selective alkyne hydrogenation are approximately the same as those described above for the selective hydrogenation of diolefins to monoolefins.

If it is desired to regenerate the catalyst of this invention after prolonged use in a hydrogenation process, this can be accomplished by leaching the spent catalyst with water to dissolve the alkali metal iodide, calcining the leached catalyst in an oxidizing atmosphere (e.g., in air; at about 500°–600° C.) to burn off carbonaceous deposits, reimpregnating the calcined catalyst with dissolved alkali metal iodide, and heating it (as is described for the fresh catalyst of this invention).

The following examples are presented to further illustrate this invention and should not be construed as unduly limiting the scope of this invention.

EXAMPLE I

This example illustrates the preparation of various palladium-containing catalysts and their use in the selective hydrogenation of 1,3-butadiene to butenes.

Catalyst A (Control) was a $Pd/Al_2O_3$ catalyst of spherical shape, which had been provided by the Calsicat Catalyst Division of Mallinckrodt Specialty Chemicals Company, Erie, Pa. under the product designation "E-143 SDU". This catalyst had a BET/$N_2$ surface area of 35 $m^2$/g, and a particle size of 1/16 inch. Catalyst A contained 0.3 weight % Pd.

Catalyst B (Control) was a $Pd/Ag/KF/Al_2O_3$ catalyst. It was prepared as follows: 80.23 grams of Catalyst A were soaked in an aqueous solution of 4.05 grams of $AgNO_3$ in 72.7 grams of distilled $H_2O$ for about 1.5 hours. Excess liquid was drained from the Ag-impregnated catalyst, which was then dried at 180° F. overnight and calcined for 3 hours at 370° C. in air. A sample of 20.18 grams of this calcined $Pd/Ag/Al_2O_3$ catalyst (labeled "Catalyst X") was then soaked with a solution of 0.47 g potassium fluoride in 14.1 cc of $H_2O$, while occasionally stirring the mixture. The thus-obtained KF-impregnated $Pd/Ag/Al_2O_3$ catalyst was dried for several hours at 180° F. and calcined in air at 370° C. for 4 hours. Catalyst B contained about 0.28 weight % Pd, about 1.6 weight % Ag, and about 1.5 weight % K (as KF).

Catalyst C (Control) was a $Pd/Ag/KI/Al_2O_3$ catalyst. It was prepared by prereducing 20.15 grams of Catalyst X (described above) for about 1 hour with $H_2$ gas at room temperature. Thereafter, the $H_2$-treated catalyst material was soaked at room temperature with a solution of 0.89 g potassium iodide in about 12.0 g distilled water. The KI-impregnated catalyst material was dried at room temperature and heated for 5 hours in nitrogen gas at 400° C. Catalyst C contained about 0.28 weight % Pd, about 2.6 weight % Ag and about 1.0 weight % K (as KI).

Catalyst D (Invention) was a $Pd/KI/Al_2O_3$ catalyst. It was prepared by prereducing 20.6 grams of Catalyst A for about 0.5 hours in a hydrogen gas stream at room temperature, and then soaking the prereduced material with a solution of 0.87 gram potassium iodide in 12.8 grams of water. The KI-impregnated catalyst material was dried over night at room temperature and then heated for about 24 hours in nitrogen gas at 400° C. Catalyst D contained about 0.3 weight % Pd and about 1.0 weight % K (as KI). It contained no Ag.

EXAMPLE II

Catalysts A–D (described above) were tested in the selective hydrogenation of 1,3-butadiene by the following procedure. About 20 cc of each catalyst was placed into a stainless steel reactor tube having an inner diameter of 0.5 inch and a length of about 18 inches. Thermocouples were inserted into the top and bottom regions of the catalyst bed, which was heated by an external furnace. The hydrocarbon feed was liquid and contained about 79 weight % 1,3-butadiene, about 13 weight % of various butenes, about 6 weight % butanes (mainly n-butane), about 0.3 weight % 1,2-butadiene, about 0.2 weight % 1-butyne and about 1.5 weight % vinylacetylene. The liquid feed rate was about 1 cc/minute in all tests. Hydrogen gas was fed with the liquid hydrocarbon feed so as to provide a $H_2$/butadiene mole ratio of about 1:1. The total pressure in the reactor was maintained at about 500 psig, and the average reaction temperature was in the range of about 100° F. to about 120° F. Generally, a portion of the reaction product was recycled to the inlet of the reactor so as to provide a volume ratio of recycle stream to fresh feed stream of about 33:1. The non-recycled product gas was analyzed at various time intervals (generally at intervals of about 1–3 hours) by means of a gas chromatograph. Pertinent test results (obtained after a steady state of the reaction was attained) are summarized in Table I.

TABLE I

| | | Average Weight Percentage of Compounds in Feed | | | | | |
|---|---|---|---|---|---|---|---|
| Feed | Catalyst | 1,3-Butadiene | 1-Butene | Cis-2-Butene | Trans-2-Butene | n-Butane | $C_6$ + Hydrocarbons |
| Feed I (for Runs 1–4) | | 78.8 | 7.6 | 2.2 | 2.8 | 6.2 | 0.06 |
| Feed II (for Runs 5–6) | | 79.1 | 7.4 | 2.2 | 2.7 | 6.1 | 0.14 |

| | | Average Weight Percentage of Compounds in Product | | | | | |
|---|---|---|---|---|---|---|---|
| Test Run | Catalyst | 1,3-Butadiene | 1-Butene | Cis-2-Butene | Trans-2-Butene | n-Butane | $C_6$ + Hydrocarbons |
| Run 1 (Control) | A ($Pd/Al_2O_3$) | 7.0 | 53.2 | 5.4 | 27.2 | 6.8 | 0.32 |
| Run 2 (Control) | B ($Pd/Ag/KF/Al_2O_3$) | 7.5 | 51.7 | 6.6 | 25.4 | 8.4 | 0.30 |
| Run 3* (Comtrol) | C ($Pd/Ag/KI/Al_2O_3$) | 60.4 | 19.8 | 3.3 | 9.4 | 6.4 | 0.28 |
| Run 4 (Invention) | D ($Pd/KI/Al_2O_3$) | 5.0 | 50.9 | 6.5 | 29.3 | 7.9 | 0.17 |
| Run 5 (Control) | A ($Pd/Al_2O_3$) | 3.3 | 52.4 | 6.9 | 28.6 | 8.1 | 0.40 |
| Run 6 (Invention) | D ($Pd/KI/Al_2O_3$) | 3.9 | 50.9 | 6.6 | 30.5 | 7.6 | 0.20 |

*No product recycle was carried out

Test data in Table I show that Invention Catalyst D consistently performed better than control Catalysts A–C, as evidenced by lower yields of "heavies" ($C_6+$ hydrocarbons, i.e., hydrocarbons containing at least 6 carbon atoms per molecule), which tend to accumulate on the catalyst surface and contribute to the gradual deactivation of the catalyst.

EXAMPLE III

This example illustrates the selective hydrogenation of dicyclopentadiene to dihydrodicyclopentadiene in the presence of various alumina-supported palladium catalysts (described in Example I).

Hydrogenation tests were carried out as follows. A stainless steel reactor tube (total length: about 18 inches; inner diameter: 0.5 inch) was filled with a bottom layer of about 20–30 cc of "36-grit" Alundum® (alumina having a surface area of less than 1 $cm^2/g$), a middle layer of about 20 cc of a particular Pd-containing catalyst, and a top layer of about 20–30 cc of "36-grit" Alundum®. Glass wool was placed below each of the two Alundum® layers and the catalyst layer. Each employed catalyst was activated by passing hydrogen gas (flow rate: 100 cc $H_2$ per minute) for 2 hours through the reactor at a temperature of 100° F. Thereafter, a solution of 10 weight % dicyclopentadiene (DCP) in cyclohexane was introduced (in a downflow mode) into the reactor at a rate of about 1 cc per minute, together with hydrogen gas as cofeed. The $H_2$ flow rate generally ranged from about 10 cc/minute to about 50 cc/minute, and the reaction temperature generally ranged from about 100° F. to about 150° F. No product recycle was carried out. The liquid product effluent (i.e., the cyclohexane-diluted product) was analyzed by means of a gas chromatograph at various time intervals (generally at 0.5–1 hour intervals). Pertinent test data are summarized in Table II.

EXAMPLE IV

In this example, the production of additional $Pd/Al_2O_3$-containing catalysts is described.

Catalyst A1 (Control) was essentially the same as Catalyst A ($Pd/Al_2O_3$, described in Example I,) except that Catalyst A1 contained about 0.5 weight % Pd (in lieu of 0.3 weight % Pd). It was supplied by the Calsicat Catalyst Division of Mallinckrodt, Specialty Chemicals Company, Erie, Pa., under the product designation "E-144 SDU".

Catalyst B1 (Control) was essentially the same as Catalyst B ($Pd/Ag/KF/Al_2O_3$, described in Example I) except that it contained about 0.5 weight % Pd (in lieu of about 0.3 weight % Pd). It was prepared substantially in accordance with the method described for Catalyst B, except that Catalyst A1 was used as the starting material (in lieu of Catalyst A). Catalyst B1 contained about 0.5 weight Pd, about 2.6 weight % Ag and about 2.6 weight % K.

Catalyst B2 (Control) was a $Pd/KF/Al_2O_3$ catalyst containing about 0.5 weight % Pd and about 2.5 weight % K. It was essentially the same as Catalyst B1, except that no silver was present. It was prepared by impregnating 20.6 grams of Catalyst A1 ($Pd/Al_2O_3$; described above) with a solution of 0.75 grams of potassium fluoride in 12.0 grams of water, followed by drying overnight at 71° C. (160° F.) and calcining for 2 hours at 380° C.

Catalyst C1 (Control) was essentially the same as Catalyst C ($Pd/Ag/KI/Al_2O_3$ described in Example I) except that Catalyst C1 contained about 0.5 weight % Pd (in lieu of 0.3 weight % Pd). It was prepared essentially in accordance with the preparation method for Catalyst C except that Catalyst A1 (in lieu of Catalyst A) was used for preparing the starting material (labeled "Catalyst X1"), which was then used to make Catalyst C1. Catalyst C1 contained about 0.5 weight % Pd, about 2.6 weight % Ag and about 1.6 weight % K.

TABLE II

| | | | | Average Content (Wt. %) of Compound in Reactor Effluent | | |
|---|---|---|---|---|---|---|
| Run | Catalyst | Reaction Temp. (°C.) | $H_2$ Flow Rate (cc/min) | Dicyclopentadiene | Dihydro-dicyclopentadiene | Tetrahydro-dicyclopentadiene |
| 7 (Control) | A ($Pd/Al_2O_3$) | 133 | 45 | 0.05 | 0.2 | 9.0 |
| | | 143 | 45 | 0.15 | 0.5 | 9.4 |
| 8 (Control) | B ($Pd/Ag/KF/Al_2O_3$) | 114 | 30 | 0.06 | 2.2 | 6.2 |
| 9 (Invention) | D ($Pd/KI/Al_2O_3$) | 107 | 30 | 1.9 | 4.0 | 3.4 |
| | | 107 | 45 | 1.9 | 4.1 | 3.1 |
| | | 132 | 45 | 0.9 | 4.3 | 3.3 |
| | | 142 | 45 | 0.8 | 4.4 | 3.3 |
| 10 (Control) | A* ($Pd/Al_2O_3$) | 107 | 25 | 0.03 | 0.3 | 7.3 |
| | | - | | | | |
| 11 (Invention) | D* ($Pd/KI/Al_2O_3$) | 103 | 30 | 0.9 | 8.6 | 0.3 |
| | | 125 | 45 | 1.0 | 8.3 | 0.3 |
| | | 145 | 50 | 0.2 | 8.3 | 0.5 |

*Catalyst was soaked for about 16 hours at room temperature in gasoline containing about 30 ppm sulfur (mainly thiophene), and was dried before the test.

Test data in Table II show that in Run 9 which employed invention Catalyst D, the yield of the desired dihydrodicyclopentadiene was much higher than in Runs 7 and 8 employing control Catalysts A and B. When invention Catalyst D had been treated with sulfur compounds, before it was used for the hydrogenation of dicyclopentadiene, the selectivity to dihydrodicyclopentadiene was even higher than that achieved with untreated Catalyst D (Run 11 vs. Run 9), whereas the sulfur-treated Catalyst A was still far inferior in terms of selectivity to dihydrodicyclopentadiene (Run 10).

Catalyst D1 (Invention) was a $Pd/KI/Al_2O_3$ catalyst (similar to Catalyst D, described in Example I). Catalyst D1 was prepared by prereducing 40.3 g of Catalyst A1 for about 40 minutes in a hydrogen stream at room temperature, impregnating the prereduced material with a solution of 1.50 g of potassium iodide in 24.0 g distilled $H_2O$, drying the KI-impregnated material at room temperature, and heating it in a nitrogen stream at 380° C. for about 4 hours. Catalyst D1 contained about 0.5 weight % Pd, about 0.7 weight % K and about 2.1 weight % I.

Catalyst D2 (Invention) was essentially the same as Catalyst D1, except that 0.67 g KI was used (in lieu of 1.50 g KI) and the final heating of the Pd/KI/Al$_2$O$_3$ material was carried out for 3 hours in hydrogen gas at 400° C. (rather than in N$_2$ at 380° C.).

Catalyst D3 (Invention) was a Pd/KI/Al$_2$O$_3$ which was prepared using KIO$_3$ instead of KI. A sample of 40.3 grams of Catalyst A1 was soaked for about 45 minutes with a solution of 0.45 g potassium iodate in 21.7 g water. The KIO$_3$-impregnated Pd/Al$_2$O$_3$ material was dried for several days at 180° F. and was then treated for 4 hours in a hydrogen gas stream at 404° C. (so as to substantially reduce KIO$_3$ to KI). Catalyst D3 contained about 0.5 weight % Pd and about 0.2 weight % K.

EXAMPLE V

This example illustrates the selective hydrogenation of C$_5$+ diolefins (contained as minor components in aromatic-rich pyrolysis gasoline) employing catalysts described in Example IV.

The feeds employed in the following hydrogenation tests were refinery streams (from an ethane pyrolysis reactor) called "debutanized aromatic concentrate" (DAC). Approximate compositions of three feeds are listed in Table III.

TABLE III

| Compound | Weight Percentage of Compounds | | |
|---|---|---|---|
|  | Feed III | Feed IV | Feed V |
| 1-Pentene | 0.9 | 1.2 | 2.6 |
| 2-Pentene | 0.2 | 0.3 | 0.7 |
| Isoprene | 0.9 | 2.0 | 3.7 |
| 1,3-Pentadiene | 0.9 | 1.5 | 3.1 |
| 1,4-Pentadiene | 0.3 | 0.6 | 1.1 |
| 1,3-Cyclopentadiene | 1.4 | 2.1 | 2.7 |
| Cyclopentene | 0.9 | 1.4 | 2.8 |
| Benzene | 73.3 | 67.7 | 54.0 |
| Toluene | 4.4 | 1.4 | 11.2 |
| Ethylbenzene | 0.3 | <0.1 | 0.7 |
| Styrene | 1.7 | 2.1 | 3.0 |
| Dicyclopentadiene | 7.6 | 9.0 | 0.2 |
| Heavies | 1.3 | 1.7 | 0.2 |
| Sulfur | -* | ~0.001 | 0.01 |

Note:
Feed V was a light (overhead) DAC fraction from which dicyclopentadiene and heavies had been substantially removed (by fractional distillation).
*Not determined (estimated to be 0.002–0.005 weight % S).

The above-described feed was hydrogenated substantially in accordance with the procedure described in Example II, except that no product recycle was carried out. The temperature and the hydrogen flow were adjusted to hydrogenate about 80% of styrene contained in the feed (mainly to ethylbenzene), so as to operate tests employing different catalysts at conditions of comparable hydrogenation severity. Generally, the reaction temperature was about 120°–250° F., the reaction pressure was about 350–500 psig, and the H$_2$ flow rate was about 25–125 cc/minute. The cooled liquid reactor effluent was analyzed by means of a gas chromatograph. Pertinent test data are summarized in Table IV.

TABLE IV

| Run | Catalyst | Feed | Average Weight Percentage of Component in Feed Product[1] | | | | | | |
|---|---|---|---|---|---|---|---|---|---|
|  |  |  | Aliphatic Pentadienes | Aliphatic Pentenes | 1,3-Cyclopentadiene | Cyclopentene | Dicyclopentadiene | Dihydrodicyclopentadiene | Tetrahydrodicyclopentadiene |
| 12 (Control) | A1 (Pd/Al$_2$O$_3$) | III | ~0 | 2.0 | 0.1 | 0.4 | 1.2 | 4.2 | 2.5 |
| 13 (Control) | C1 (Pd/Ag/KI/Al$_2$O$_3$) | III | —[2] | —[2] | —[2] | —[2] | —[2] | —[2] | —[2] |
| 14 (Invention) | D1 (Pd/KI/Al$_2$O$_3$) | III | <0.1 | 2.5 | <0.1 | 0.9 | 0.2 | 8.0 | 0.4 |
| 15 (Control) | B1 (Pd/Ag/KF/Al$_2$O$_3$) | IV | 0.1 | 4.0 | 0.2 | 1.0 | 2.1 | 6.0 | 1.4 |
| 16 (Control) | B2 (Pd/KF/Al$_2$O$_3$) | IV | 0.1 | 3.7 | 0.1 | 0.8 | 1.8 | 5.8 | 2.2 |
| 17 (Invention) | D1 (Pd/KI/Al$_2$O$_3$) | IV | 0.1 | 4.7 | <0.1 | 1.7 | 0.6 | 8.5 | 0.4 |

[1]Product formed at reaction conditions selected to achieve ~80% conversion of styrene (to ethylbenzene).
[2]Catalyst was not active enough to achieve 80% conversion of styrene.

Test data in Table IV clearly show that Runs 14 and 17 employing invention Catalyst D1 (Pd/KI/Al$_2$O$_3$) produced the desired monoolefins (aliphatic pentenes, cyclopentene and dihydrodicyclopentadiene) at higher yields than runs employing control catalysts. Thus, the invention catalyst exhibited higher selectivity to monoolefins than various Pd-containing control catalysts.

Results of three additional test runs (not included in Table IV) employing Feed V and operating at such conditions as to achieve a styrene conversion of 90–95% indicated that invention Catalysts D2 and D3 (described in Example IV) achieved almost complete conversions of aliphatic pentadienes to pentenes and of cyclopentadienes to cyclopentene, whereas control Catalyst A1 was considerably less selective to the C$_5$ monoolefins.

Results of two month-long comparative tests for hydrogenating a prefractionated debutanized aromatic concentrate (DAC), which was similar to Feed V, employing an invention catalyst and a control catalyst are shown in FIG. 1. In both tests, the feed contained about 2.3–2.5 weight % aliphatic C$_5$ monoolefins and about 5.7–5.9 weight % aliphatic C$_5$ diolefins. The graphs in FIG. 1 demonstrate that the invention catalyst (Pd/KI/Al$_2$O$_3$, essentially the same as Catalyst D2) was considerably more selective to C$_5$ monoolefins than a corresponding control catalyst (Pd/Al$_2$O$_3$, essentially the same as Catalyst A1), and exhibited excellent stability over a time period spanning from the fifth day to the thirtieth day of the hydrogenation reaction. Both tests were run at such conditions as to attain approximately 80° to about 100° F. A major portion of the product was recycled to the reactor. The rate of recycled product to fresh propane feed was about 6:1. Product samples were analyzed by means of a gas chromatograph. Pertinent test results are summarized in Table V.

TABLE V

| Catalyst | H$_2$ Flow Rate (cc/minute) | Content of Component in Product (Weight %) | | | | | | % Conversion | | |
|---|---|---|---|---|---|---|---|---|---|---|
| | | Propylene | PD[1] | MA[2] | Butenes | Butadiene | C$_6$[+3] | MA[2] | PD[1] | (MA + PD) |
| A (Control) | 15 | 2.98 | 0.63 | 0.73 | 0.11 | 0.18 | 0.28 | 71.6 | 42.1 | 63.0 |
| B3 (Control) | 15 | 3.48 | 0.43 | 0.55 | 0.18 | 0.10 | 0.25 | 78.8 | 60.1 | 73.3 |
| D4 (Invention) | 15 | 3.25 | 0.67 | 0.59 | 0.11 | 0.17 | 0.06 | 77.3 | 38.3 | 65.8 |
| A (Control) | 20 | 3.90 | 0.18 | 0.25 | 0.22 | 0.06 | 0.42 | 90.6 | 83.1 | 88.4 |
| B3 (Control) | 20 | 4.13 | 0.16 | 0.17 | 0.25 | 0.04 | 0.29 | 93.5 | 85.4 | 91.1 |
| D4 (Invention) | 20 | 4.14 | 0.38 | 0.17 | 0.18 | 0.11 | 0.07 | 93.3 | 65.0 | 85.0 |
| A (Control) | 25 | 3.19 | 0.08 | 0.10 | 0.23 | 0.03 | 0.39 | 96.1 | 92.4 | 95.0 |
| B3 (Control) | 25 | 3.93 | 0.04 | 0.13 | 0.25 | 0.01 | 0.21 | 99.5 | 96.0 | 98.5 |
| D4 (Invention) | | 4.35 | 0.07 | 0.00 | 0.26 | 0.02 | 0.05 | 100.0 | 93.8 | 98.2 |
| A (Control) | 30 | 2.84 | 0.05 | 0.02 | 0.24 | 0.02 | 0.35 | 99.2 | 95.3 | 98.1 |
| B3 (Control) | 30 | 3.55 | 0.01 | 0.00 | 0.24 | 0 | 0.14 | 100.0 | 99.2 | 99.8 |
| D4 (Invention) | 30 | 3.61 | 0.01 | 0.00 | 0.26 | 0 | 0.05 | 100.0 | 99.0 | 99.7 |

[1]propadiene
[2]methylacetylene
[3]hydrocarbons containing 6 or more than 6 carbon atoms per molecule.
Note: The propane content in the product was about the same in all runs (about 95–96 weight %).

the same styrene conversion (about 92–95%). At these conditions, essentially complete conversion of all aliphatic C$_5$ diolefin was achieved. The most pertinent reaction conditions of the run employing the invention catalyst (Pd/KI/Al$_2$O$_3$) were: reaction temperature of 170°–210° F., reaction pressure of 340–360 psig, DAC feed rate of 0.9–1.1 cc/minute, and H$_2$ feed rate of 65–75 cc/minute. A portion of the reaction product was recycled to the inlet of the reactor so as to provide a volume ratio of recycle stream to fresh feed stream of about 1:1.

EXAMPLE VI

This example illustrates the selective hydrogenation of an alkyne (methylacetylene, MA), in conjunction with diolefins (in particular propadiene, PD) contained in a propane feed (from a commercial ethylene plant).

The following catalysts were employed in comparative hydrogenation runs: Catalyst A (Pd/Al$_2$O$_3$; containing about 0.3 weight % Pd; see Example I); Catalyst B3 (PdAg/KF/Al$_2$O$_3$) which was prepared substantially in accordance with the method for preparing Catalyst B and contained about 0.3 weight % Pd, about 1.4 weight % Ag, and about 1.3 weight % K as KF; see Example I); and Catalyst D4 (Pd/KI/Al$_2$O$_3$) which was prepared substantially in accordance with the procedure for Catalyst D3 (described in Example IV), except that Catalyst D4 contained 0.3 weight % Pd and 0.48 weight % K (as KI).

Figure 2:
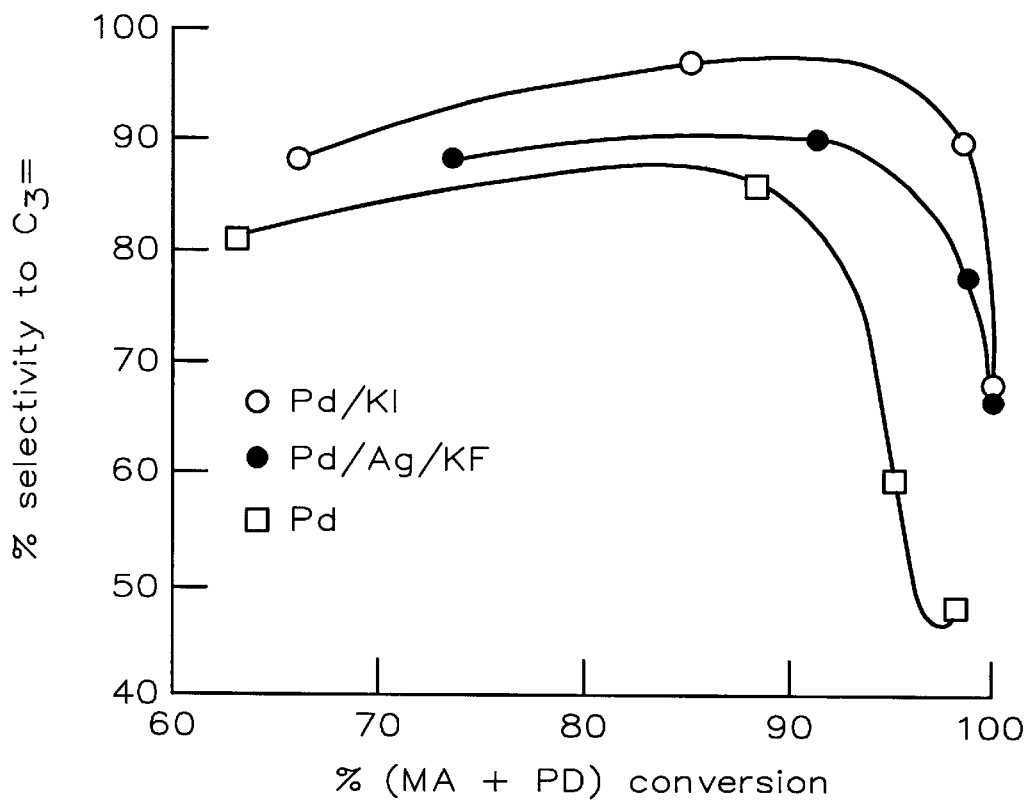
FIG. 2 shows the selectivity to propylene in a selective hydrogenation of acetylene at different conversions of methylacetylene and propadiene.
Figure 3:
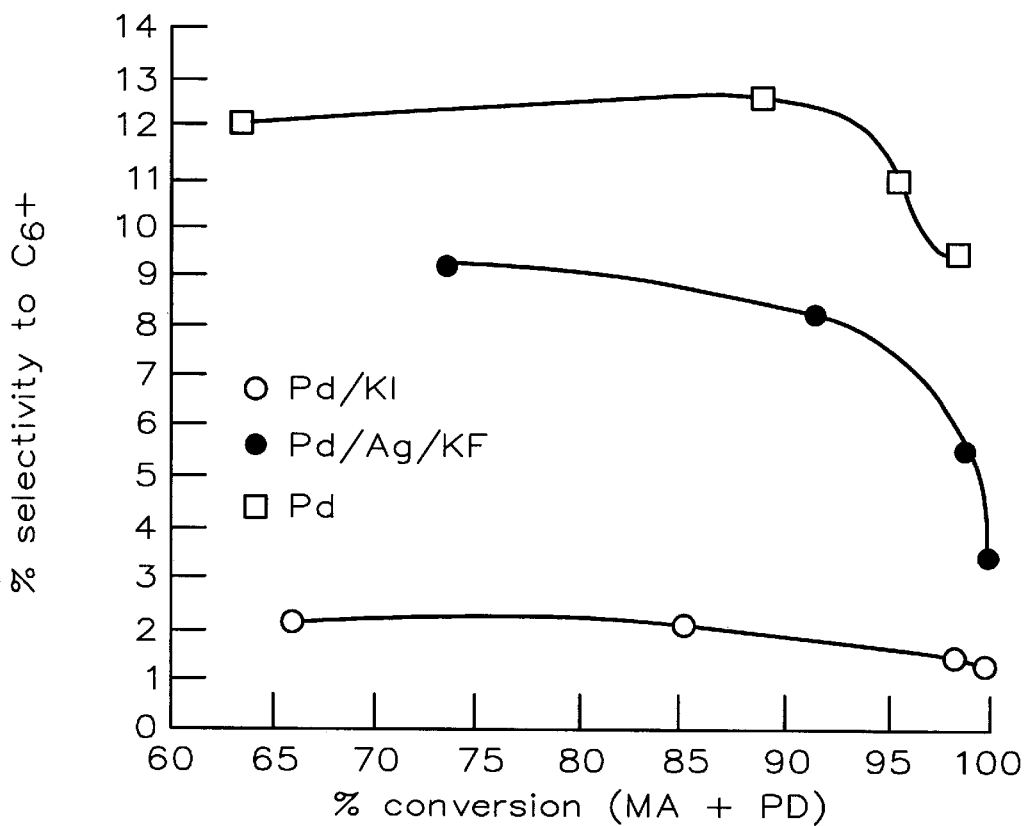
FIG. 3 shows the selectivity to $C_6+$ hydrocarbons in a selective hydrogenation of acetylene at different conversions of methylacetylene and propadiene.

The hydrogenation tests were carried out substantially in accordance with the procedure described in Example II, except that a liquefied propane feed was used. This propane feed contained 94.65 weight % propane, 1.10 weight % propylene, 1.08 weight % propadiene (PD), 2.60 weight % methylacetylene (MA, propyne), 0.07 weight % 1-butene, 0.21 weight % butadienes, and traces of C$_6$+ hydrocarbons. The feed rate of fresh liquid propane was about 1.4 cc/minute, the H$_2$ feed rate was in the range of about 15 to about 30 cc/minute, the reaction pressure was about 320 psig, and the reaction temperature was in the range of about Test data in Table V show that the Pd/KI/Al$_2$O$_3$ catalyst of this invention (Catalyst D4) consistently produced less undesirable heavies (C$_6$+ hydrocarbons) than the two control catalysts, at comparable conversions of (MA+PD). Selectivities to desirable propylene and to undesirable C$_6$+ hydrocarbons, respectively, at various (MA+PD) conversions are presented in FIG. 2 and FIG. 3, respectively. The selectivities were calculated by dividing the yield of a product component by the combined conversion of MA (methylacetylene) and PD (propadiene). These figures indicate that the catalyst of this invention (Pd/KI/Al$_2$O$_3$) consistently converted methylacetylene and propadiene at a higher selectivity to propylene (a desired product) and at a lower selectivity to undesirable C$_6$+ hydrocarbons than the two control catalysts, at equal (MA+PD) conversions.

Reasonable variations, modifications and adaptations for various usages and conditions can be made within the scope of the disclosure and the appended claims, without departing from the scope of this invention.

That which is claimed is:

1. A process comprising contacting a fluid which comprises a highly unsaturated hydrocarbon, in the presence of hydrogen, with a catalyst composition under a condition effective to convert said highly unsaturated hydrocarbon to a less unsaturated hydrocarbon wherein said catalyst composition consists essentially of a palladium-containing material selected from the group consisting of palladium metal, palladium oxides, and combinations of two or more thereof, an alkali metal iodide, and an inorganic support material.

2. A process according to claim 1 wherein said fluid further comprises an alkene.

3. A process according to claim 2 wherein said alkene is selected from the group consisting of ethylene, propylene, butenes, and mixtures of two or more thereof.

4. A process according to claim 2 wherein said alkene is ethylene.

5. A process according to claim 1 wherein said inorganic support material is selected from the group consisting of alumina, silica, titania, zirconia, aluminosilicates, zinc aluminate, zinc titanate, and mixtures of two or more thereof.

6. A process according to claim 1 wherein said alkali metal iodide is potassium iodide and said inorganic support material is alumina.

7. A process according to claim 2 wherein said alkali metal iodide is potassium iodide and said inorganic support material is alumina.

8. A process according to claim 1 wherein said catalyst composition contains about 0.01 to about 2 weight % palladium and about 0.02 to about 10 weight % of an alkali metal.

9. A process according to claim 2 wherein said catalyst composition contains about 0.01 to about 2 weight % palladium and about 0.02 to about 10 weight % of an alkali metal.

10. A process according to claim 8 wherein said alkali metal is potassium and said inorganic support material is alumina.

11. A process according to claim 9 wherein said alkali metal is potassium and said inorganic support material is alumina.

12. A process according to claim 2 wherein said catalyst composition contains about 0.05 to about 1 weight % palladium and about 0.05 to about 5 weight % potassium, and has a surface area of about 1 to about 200 m$^2$/g.

13. A process according to claim 1 wherein said highly unsaturated hydrocarbon is selected from the group consisting of diolefins, alkynes, and mixtures of two or more thereof.

14. A process according to claim 13 wherein said diolefin is selected from the group consisting of propadiene, propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene, and mixtures of two or more thereof.

15. A process according to claim 13 wherein said diolefin is selected from the group consisting of propadiene, 1,3-butadiene, 1,3-pentadiene, 1,4-pentadiene, isoprene, 1,3-cyclopentadiene, dicyclopentadiene, and mixtures of two or more thereof.

16. A process according to claim 2 wherein said highly unsaturated hydrocarbon is selected from the group consisting of propadiene, 1,3-butadiene, 1,3-pentadiene, 1,4-pentadiene, isoprene, 1,3-cyclopentadiene, dicyclopentadiene, and mixtures of two or more thereof.

17. A process according to claim 13 wherein said alkyne is selected from the group consisting of acetylene, propyne, 1-butyne, 2-butyne, 1-pentyne, 2-pentyne, 3-methyl-1-butyne, 1-hexyne, 1-heptyne, 1-octyne, 1-nonyne, 1-decyne, and mixtures of two or more thereof.

18. A process according to claim 13 wherein said alkyne is acetylene.

19. A process according to claim 2 wherein said highly unsaturated hydrocarbon is acetylene.

20. A process in accordance with claim 13 wherein said fluid further comprises 50 to 90 weight % of aromatic hydrocarbons.

21. A process in accordance with claim 2 wherein said fluid further comprises 50 to 90 weight % of aromatic hydrocarbons.

22. A process comprising contacting an alkene fluid stream which comprises a highly unsaturated hydrocarbon, in the presence of hydrogen, with a catalyst composition under a condition effective to convert said highly unsaturated hydrocarbon to a less unsaturated hydrocarbon wherein said catalyst composition consists essentially of a palladium-containing material selected from the group consisting of palladium metal, palladium oxides, and combinations of two or more thereof, an alkali metal iodide, and an inorganic support material;

said alkene is selected from the group consisting of ethylene, propylene, butenes, and mixtures of two or more thereof;

said inorganic support material is selected from the group consisting of alumina, silica, titania, zirconia, aluminosilicates, zinc aluminate, zinc titanate, and mixtures of two or more thereof;

said catalyst composition contains about 0.01 to about 2 weight % palladium and about 0.02 to about 10 weight % of an alkali metal; and said highly unsaturated hydrocarbon is selected from the group consisting of diolefins, alkynes, and combinations of two or more thereof.

23. A process according to claim 22 wherein said highly unsaturated hydrocarbon is selected from the group consisting of propadiene, propadiene, 1,2-butadiene, 1,3-butadiene, isoprene, 1,2-pentadiene, 1,3-pentadiene, 1,4-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, methylhexadienes, octadienes, methylheptadienes, dimethylhexadienes, ethylhexadienes, trimethylpentadienes, methyloctadienes, dimethylheptadienes, ethyloctadienes, trimethylhexadienes, nonadienes, decadienes, undecadienes, dodecadienes, cyclopentadienes, cyclohexadienes, methylcyclopentadienes, cycloheptadienes, methylcyclohexadienes, dimethylcyclopentadienes, ethylcyclopentadienes, dicyclopentadiene, acetylene, propyne, 1-butyne, 2-butyne, 1-pentyne, 2-pentyne, 3-methyl-1-butyne, 1-hexyne, 1-heptyne, 1-octyne, 1-nonyne, 1-decyne, and mixtures of two or more thereof.

24. A process according to claim 22 wherein said catalyst composition contains about 0.05 to about 1 weight % palladium and about 0.05 to about 5 weight % potassium, and has a surface area of about 1 to about 200 m$^2$/g; and said highly unsaturated hydrocarbon is selected from the group consisting of acetylene, propadiene, 1,3-butadiene, 1,3-pentadiene, 1,4-pentadiene, isoprene, 1,3-cyclopentadiene, dicyclopentadiene, and mixtures of two or more thereof.

25. A process in accordance with claim 22 wherein said alkene fluid stream further comprises 50 to 90 weight % of aromatic hydrocarbons.

26. A process according to claim 22 wherein said alkene is ethylene.

27. A process according to claim 22 wherein palladium is distributed on the surface of said inorganic support.

28. A selective hydrogenation process comprising contacting a fluid stream which comprises ethylene and a highly unsaturated hydrocarbon, in the presence of hydrogen, with a catalyst composition under a condition effective to convert said highly unsaturated hydrocarbon to a less unsaturated hydrocarbon wherein said catalyst composition consists essentially of a palladium-containing material selected from the group consisting of palladium metal, palladium oxides, and combinations of two or more thereof, an alkali metal iodide, and an inorganic support material;

said alkali metal iodide is potassium iodide and said inorganic support material is alumina;

said catalyst composition contains about 0.05 to about 1 weight % palladium and about 0.05 to about 5 weight % potassium, and has a surface area of about 1 to about 200 m$^2$/g;

said highly unsaturated hydrocarbon is selected from the group consisting of acetylene, propadiene, 1,3-butadiene, 1,3-pentadiene, 1,4-pentadiene, isoprene, 1,3-cyclopentadiene, dicyclopentadiene, and mixtures of two or more thereof;

said process is carried out at a temperature in the range of about 30° to about 200° C. and under a pressure in the range of about 15 to about 2000 psig; and about 1 to about 2 moles of hydrogen are employed for each mole of said highly unsaturated hydrocarbon present.

29. A process according to claim 28 wherein said fluid stream also comprises 50 to 90 weight % of aromatic hydrocarbons.

30. A process according to claim 13 wherein said alkyne has 2 to 12 carbon atoms per molecule and said diolefin has 3 to 12 carbon atoms per molecule.

31. A process according to claim 22 wherein said alkyne has 2 to 12 carbon atoms per molecule and said diolefin has 3 to 12 carbon atoms per molecule.

* * * * *